United States Patent
Suovaniemi et al.

(10) Patent No.: US 8,318,108 B2
(45) Date of Patent: Nov. 27, 2012

(54) SUCTION DEVICE

(75) Inventors: Osmo Suovaniemi, Helsinki (FI); Pertti Ekholm, Helsinki (FI)

(73) Assignee: Sartorius Biohit Liquid Handling Oy, Helsinki (FI)

( * ) Notice: Subject to any disclaimer, the term of this patent is extended or adjusted under 35 U.S.C. 154(b) by 0 days.

(21) Appl. No.: 12/945,718

(22) Filed: Nov. 12, 2010

(65) Prior Publication Data
US 2011/0167933 A1   Jul. 14, 2011

Related U.S. Application Data

(62) Division of application No. 10/575,377, filed as application No. PCT/FI2005/050262 on Jun. 30, 2005, now abandoned.

(30) Foreign Application Priority Data

Jul. 5, 2004   (FI) ..................................... 20040936

(51) Int. Cl.
*B01L 3/02*   (2006.01)
*G01N 1/10*   (2006.01)

(52) U.S. Cl. ........ 422/501; 422/500; 422/928; 436/180; 73/863.32; 73/864; 73/864.01; 73/864.13

(58) Field of Classification Search .......... 422/500–501, 422/509, 518, 520, 928; 73/863.32, 864, 73/864.01, 864.13; 436/180
See application file for complete search history.

(56) References Cited

U.S. PATENT DOCUMENTS

| | | | | |
|---|---|---|---|---|
| 4,228,922 | A * | 10/1980 | Takeshita | 222/47 |
| 4,966,585 | A | 10/1990 | Gangemi | |
| 5,330,717 | A | 7/1994 | Berteloot et al. | |
| 5,364,596 | A | 11/1994 | Magnussen, Jr. et al. | |
| 5,389,341 | A * | 2/1995 | Tuunanen et al. | 422/509 |
| 5,525,302 | A * | 6/1996 | Astle | 422/511 |
| 6,254,832 | B1 * | 7/2001 | Rainin et al. | 422/525 |
| 6,352,673 | B1 | 3/2002 | Rainin et al. | |
| 6,455,006 | B1 * | 9/2002 | Mukai | 422/501 |
| 6,645,433 | B2 * | 11/2003 | Homberg et al. | 422/522 |
| 6,773,927 | B2 * | 8/2004 | Osawa et al. | 436/180 |
| 6,926,866 | B2 | 8/2005 | Sickinger et al. | |
| 7,125,727 | B2 * | 10/2006 | Massaro | 436/180 |
| 2005/0118066 | A1 | 6/2005 | Ikeda et al. | |
| 2005/0214172 | A1 | 9/2005 | Burgisser | |

FOREIGN PATENT DOCUMENTS

| | | |
|---|---|---|
| EP | 0435415 A1 | 7/1991 |
| EP | 1084723 A1 | 3/2001 |
| JP | 10-501166 | 2/1998 |
| JP | 2002-236130 A | 8/2002 |
| JP | 2003-28886 A | 1/2003 |
| JP | 2003-149255 A | 5/2003 |
| JP | 2003-343426 A | 12/2003 |
| WO | WO 95/34333 | 12/1995 |
| WO | WO 00/51738 | 9/2000 |
| WO | WO 03/015846 A2 | 2/2003 |

* cited by examiner

*Primary Examiner* — Brian R Gordon
(74) *Attorney, Agent, or Firm* — Birch, Stewart, Kolasch & Birch, LLP

(57) ABSTRACT

This invention relates to plunger operated liquid dispensers, such as hand held pipettors, which are used to portion liquids. Specifically the invention relates to a reliable removal of a liquid from the liquid dispenser. According to the invention the plunger of the liquid dispenser is arranged into a speeded up movement while removing the liquid. This change in speed is preferably sudden.

4 Claims, 3 Drawing Sheets

SUCTION DEVICE

CROSS-REFERENCE TO RELATED APPLICATIONS

This application is a divisional application of application Ser. No. 10/575,377, whose §371(c) date is Apr. 11, 2006 now abandoned, and which is a National Stage Entry of PCT/FI2005/050262, filed Jun. 30, 2005, the entire contents of which are incorporated herein by reference.

BACKGROUND OF THE ART

This invention relates to plunger operated liquid dispensers, such as manual pipettors, which are used to dispense liquids. Specifically the invention relates to reliable removal of a liquid from the liquid dispenser. Especially preferable the invention relates to liquid dispensers that are used to handle relatively small sample amounts, such as around one microliter. More specifically the object of the invention is further described in the preambles of the independent claims.

Plunger operated liquid dispensers normally have a function which is called a blow-out. In a blow-out, the distance of the movement of the plunger while removing a liquid (secondary movement) is longer than the movement which has been made by the plunger while receiving the liquid. Thus removal of the liquid can be improved when compared to the situation when the plunger would move the same distance in both the receiving and removal phases. In manual pipettors this function is usually accomplished by two springs, whereas in electronic pipettors this function is possible to accomplish simply by continuing the movement of the plunger with the help of a motor. In both approaches only one plunger is used.

The aforementioned removing problem is greater with small volumes when the diameter of the plunger is small in relation to the removal opening of the tip. What usually happens is that the liquid is not entirely removed from the tip and instead revolves to the outer surface of the tip. Then the liquid drop must be mechanically removed by the user by transferring the liquid mechanically to a wall of the tube which is receiving the sample. Usually the removal pipetting has to be repeated several times. Another solution is to saturate the sample on the tip to a liquid already existing in the tube. In the end, how well the liquid actually transfers and how much still remains in the tip of the pipettor always depends on the carefulness of the person performing the pipetting. Naturally these different kinds of contacts also result in an increase in different contamination risks.

More generally the weakness in pipettors can be said to be this difficult pipetting of small portion volumes. Sample volumes below 10 µL do not come off from the pipettor tip, such that they must be pipetted saturated in a liquid or they must be able to catch on the wall of a test tube. This has resulted in that manual pipettors are used when small volumes are pipetted because manual pipettors enable several removals successively. However, the accuracy is then quite poor.

The international standards allow large CV percentages for 0.1-2.0 µL volumes. However, smaller volumes usually are portion volumes of a test sample which determine the accuracy of the whole test. These standards are clearly drafted taking into consideration the problem caused by the small plunger diameter.

Automatic dispensers which require that a different tip must be used for each sample cannot dispense small volumes, which results in that a lot of reagences must be used. In addition if attempts are made to catch the sample on the bottom of a test tube/plate with these automatic dispensers, the accuracy of the structure of this kind of device must be controlled extremely well, and in the worst case, the situation is such that a bad accuracy appears occasionally.

In turn, in hand held pipettors, especially in 10 µL pipettors, because of different attachment of the tips, catching the sample on a test plate is extremely difficult.

One approach is to use two nested plungers. The inner plunger is a portioning plunger whose movement distance defines the volume to be dispensed. The distance of the movement of this portioning plunger is the same while receiving the liquid and while removing it. The outer plunger is a blow-out plunger, which starts its movement only after the portioning plunger has carried out its removal movement.

Another approach is to use two plungers so that these two plungers act simultaneously during the removal, whereby more pressure is developed to a tip of the pipettor. However, even the smallest drops which tend the remain in the tip are desired to be removed from the tip.

SUMMARY OF THE INVENTION

Based on what is said above, now it has been noticed that the removing problems of the liquid relate to the slow movement of the plunger during the removal phase. The purpose of this invention is thus to develop further the function of the pipettors in situations where a tip of the liquid dispenser is desired to be emptied so that there is no need for contact with a test tube or with a liquid, and so that dividing of the liquid between the tube and the tip remains the same between portionings.

The teachings of the present invention in relation to the aforementioned state of the art are that the movement of the plunger of the liquid dispenser is quickened during removal of the liquid. This change in speed is preferably sudden, when the sample is to be launched out from the liquid dispenser. More specifically the invention is characterized by the characterizing parts of the independent claims. Some preferable embodiments are presented in the dependent claims.

The concept behind the invention is that the sample is portioned with one plunger in a way that the plunger is a small diameter plunger in a receiving phase and a large diameter plunger in a removal phase. The seemingly larger diameter of the plunger is provided with a multiple movement speed. The movement speed can be used in the most preferable phase to optimize portioning. The high movement speed and its activation can be accomplished with several technical components.

Electrical hand held pipettors are known to have adjustment possibilities such that the movement of the plunger can be adjusted using programs. This intrinsically is obvious for a person skilled in the art through experimentation so that an optimal movement speed can be achieved for the plunger. However, in these previously known electrical pipettors there is no difference between the receiving and removal phases such that the removal movement speed would be quickened to solve this particular problem where the sample tends to revolve to the outer surface of the tip during the removal phase, especially with small volumes. Also the previously known motors do not present such motors which could produce speeds sufficient to solve this problem.

The previously mentioned optimization of the movement speed of the plunger is a substantial part of the present invention. It is important that the receiving suction is carried out slowly and the removal movement is carried out with high speed. After what is said here it is obvious for a person skilled in the art that the mentioned removal movement speed can be achieved in several different ways. According to the invention, the liquid dispenser comprises such means which enable the removal movement of the plunger to be substantially increased. With the help of such a fast removal speed the liquid dispenser tip always empties similarly, when the CV percent is comparable also with small volumes.

According to one embodiment of the invention, the previously mentioned means comprise spring-like means, i.e., energy means, which produces the energy needed by the removal movement. Here it must be noted that the spring-like means is very preferable but such energy can also be produced also in a different way, for example, by programming in the case of an electrical pipettor. Preferably such spring-like means can be, for example, a spring, or, for example, a combination utilizing magnetic forces. According to this embodiment the spring-like means must be activated to store potential energy, after which this activation must be locked with suitable means. Such activation can be implemented, again as an example, using magnetic forces. Naturally this embodiment also requires means which can release the said activation of the spring-like means and thus release the potential energy stored therein. Such release means can be, for example, a mechanical trigger which may utilize the possible magnetic forces.

According to one preferable embodiment the liquid dispenser is an electronic pipettor, such as, for example, a Biohit eLine-series pipettor. A pipettor comprises a cylinder part which is adapted inside a body, inside which cylinder part a plunger moves to dispense liquid. The plunger has a normal relatively slow movement speed produced by the motor. To implement the invention the pipettor is equipped with launch means. These launch means comprise an actuator shaft, which is preferably made of magnetic steel. In addition the launch means comprise a spring, a magnet, and activation means, which is preferably an activation pin, or similarly functioning mechanical member. To carry out the invention, first the actuator shaft comes into contact with the magnet. At this point the launch spring is activated, storing potential energy. After this the sample is received normally by moving the plunger upwards. When the required liquid volume has been received, the plunger stops. When the liquid needs to be removed from the sample space, the motor starts again an upward movement of the plunger. When the movement continues upwards, the launch pin comes into contact with a flange surface, which is preferably provided in the pipettor body. When the movement of the plunger continues upwards, the launch pin, pushed by the contact with the flange, forces the actuator shaft apart from the magnet, releasing the spring from its locked state. The energy released by the spring then forces the actuator shaft in a fast downward movement, such that the actual suction plunger causes fast movement of the liquid from the sample space when moving downwards. In this manner, the liquid does not revolve to the outer wall of the tip but is instead entirely removed from the tip, which is, for example, a detachable disposable tip.

In another embodiment the present invention is a hand held mechanical pipettor. In a mechanical pipettor the activation of an energy means (i.e., storage of potential energy) can be carried out, for example, similarly as described above during a downward movement of a plunger, which movement can be, for example, a mechanical blow-out movement. After the energy means is activated, the sample is then received normally. Finally the energy means is launched (i.e., its potential energy is released) with appropriate means. Such appropriate means can be, for example, a trigger provided in the pipettor body.

BRIEF DESCRIPTION OF THE SEVERAL VIEWS OF THE DRAWINGS

In the following reference is made to the attached drawings where is presented one way for implementing the invention. In the drawings.

DETAILED DESCRIPTION OF THE INVENTION

Figure 1:
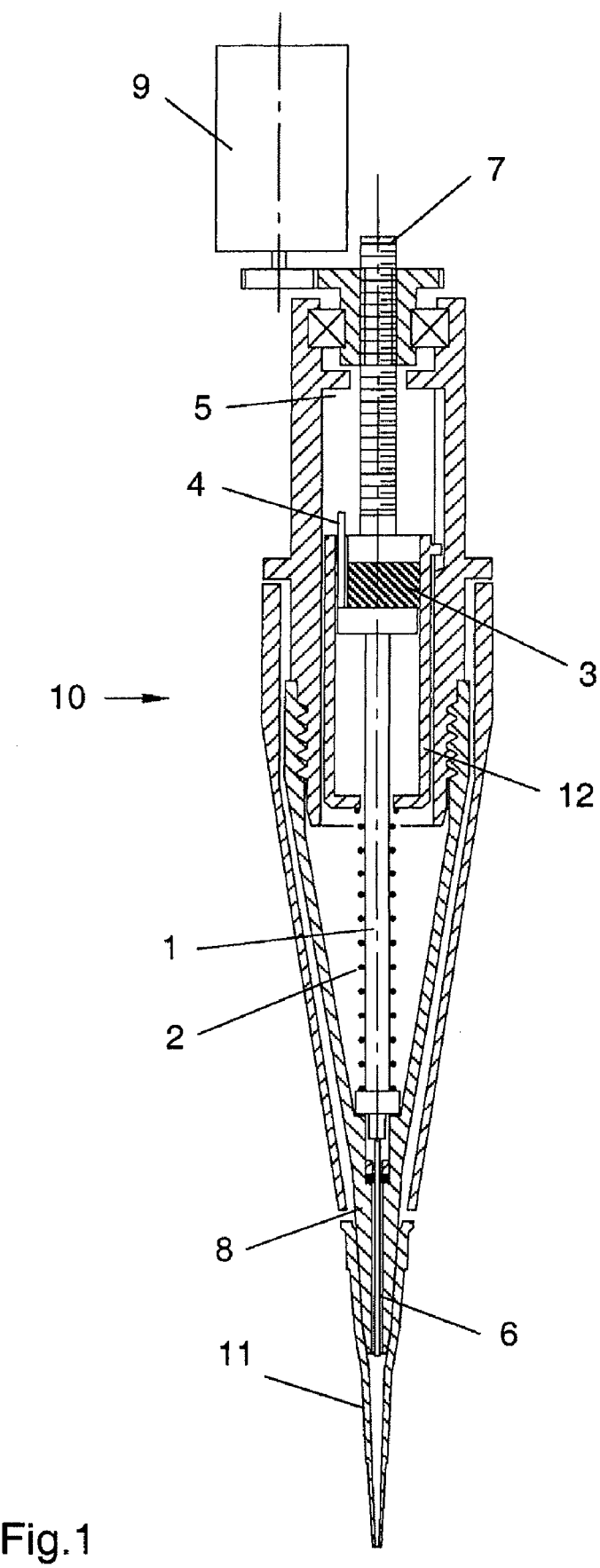
FIG. 1 depicts a simplified cross section drawing of a hand held pipettor.
Figure 2:
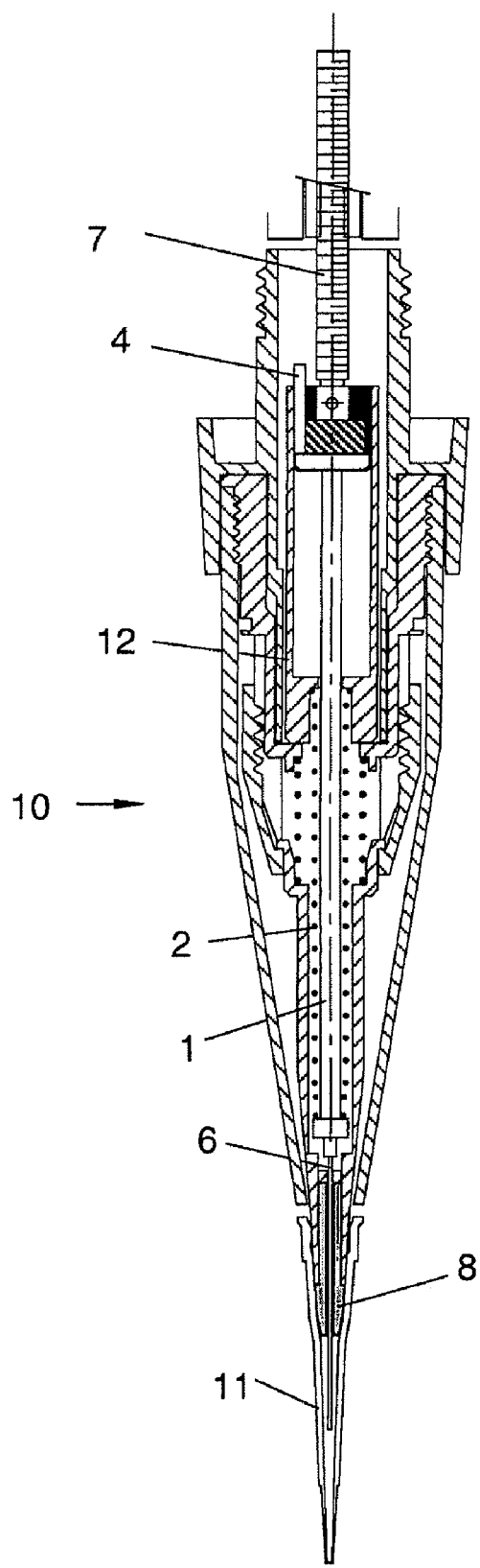
FIG. 2 depicts slightly more details of the pipettor of FIG. 1.

Similar numbering is used throughout the figures for the parts which are included in several figures. Pipettor 10 comprises an inner actuator shaft 1, a spring 2, a magnet 3, a launch pin 4, an upper flange 5, a suction plunger 6, a function plunger 7, a cylinder 8, a motor 9, a disposable tip 11 and a launch means body 12.

The actual actuator implementing the present invention comprises in these figures the actuator shaft, the magnet and the launch pin.

The suction plunger 6 is connected to the actuator shaft 1, which is connected to the function plunger 7 by the magnet 3. When the motor 9 moves the shaft of the function plunger 7 upwards, the actuator shaft 1, the suction plunger 6, and the function plunger 7 move together and the shaft of the suction plunger 6 moves inside the cylinder 8 causing the suction function for receiving a sample to the tip. One end of the spring 2 is connected to a lower end of launch means body 12, and the other end spring 2 is connected to a flange in a lower part of actuator shaft 1. The magnet 3 is solidly inside the launch means body 12, and the actuator shaft 1 is arranged to move inside the launch means body 12. The launch pin 4 is arranged so that when it comes into contact with the upper flange 5 arranged in the pipettor body, it forces the actuator shaft 1 apart from the magnet 3 inside the launch means body 12.

Figure 3:
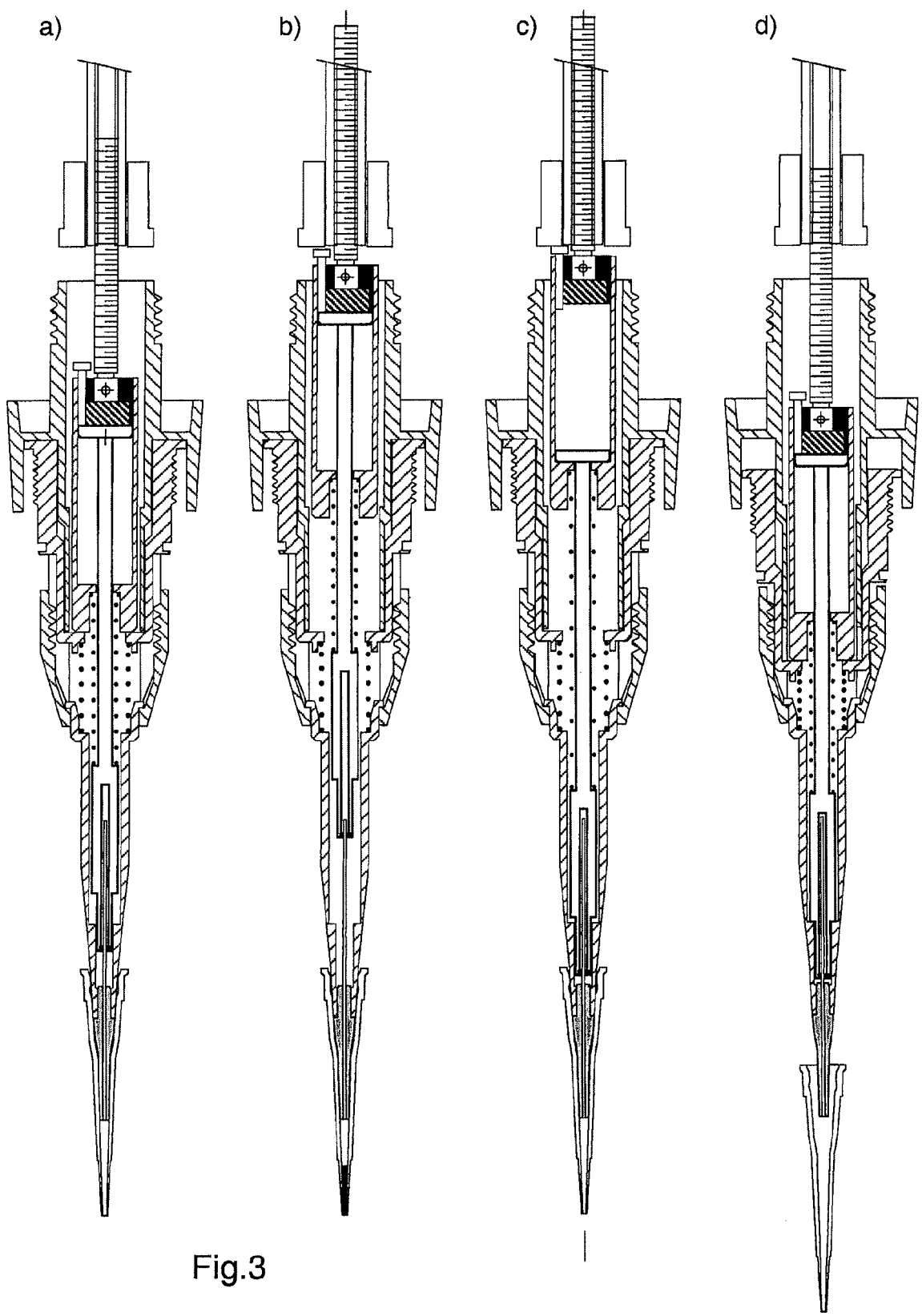
FIG. 3 presents pictures a-d which depicts pipettor of FIG. 2 in action.

The object of the invention is that the volume to be portioned is launched out with high speed. When implementing the structure it is important that the home position of the suction plunger 6 is located so that the suction movement fits before the launch point. This home is especially presented in FIG. 3a. Then according to the invention the sample is received in the tip, which position is presented in FIG. 3b. After this the function plunger 7 is driven slightly more upwards such that the launch pin 4 contacts the upper flange 5 and pushes the actuator shaft 1 apart from the magnet 3. The contact between the launch pin 4 and the upper flange 5 is also presented in FIG. 3b. When the actuator shaft 1 has been separated from the magnet 3, the released spring forces the actuator shaft 1, and consequently suction plunger 6, to shoot downwards with high speed as is presented in FIG. 3c. In hand held electronic pipettors removal of the tip can be preferably carried out during the activation of the actuator for a new suction function. Such activation of the actuator is presented in FIG. 3d, where the function plunger 7 is driven to push the launch means body 12 downwards until the magnet 3 again comes in contact with the actuator shaft 1.

The invention claimed is:

1. A liquid dispenser for receiving and dispensing a sample, which comprises:
   a body part;
   a cylinder part arranged inside the body part;

a suction plunger movably arranged inside the cylinder part; and a function plunger disposed at an upper part of the body part of the liquid dispenser and detachably connectable to the suction plunger, wherein the sample is received into the liquid dispenser by a receiving movement of the suction plunger at a first speed in a connected state with the function plunger, and the sample is dispensed from the liquid dispenser by an emptying movement of the suction plunger at a second speed greater than the first speed in a disconnected state from the function plunger, the liquid dispenser further comprising:

an energy storing device for providing energy to move the suction plunger during the emptying movement;

a locking device for locking the energy storing device from releasing the energy;

a launch device for releasing the locking device such that the energy is provided to move the suction plunger during the emptying movement, wherein:

the energy storing device is a spring; and the locking device is a magnet, wherein the launch device further comprises:

an actuator shaft with a magnetic property and which has a lower part and an upper part, wherein the actuator shaft is disposed such that the lower part of the actuator shaft is connected to the suction plunger and the upper part of the actuator shaft is connectable to a lower part of the function plunger via the magnet;

a launch body which accommodates the upper part of the actuator shaft and the magnet;

a launch pin disposed at an upper part of the launch body; and an upper flange disposed in the upper part of the body part, wherein the suction plunger is disposed at a lower part of the body part, the spring is arranged to be strained between the launch body and the actuator shaft, and the launch pin, the upper flange, and the spring are arranged so that when the function plunger is moved upward in relation to the body part until the launch pin contacts the upper flange, the contact between the launch pin and the upper flange causes separation of the actuator shaft from the magnet, whereby the spring forces the actuator shaft in a downward movement to effect the emptying movement of the suction plunger at the second speed.

2. The liquid dispenser according to claim 1, wherein the liquid dispenser is an electronic dispenser, and the liquid dispenser further comprises a motor which drives the receiving movement of the function plunger and the suction plunger.

3. The liquid dispenser according to claim 1, wherein the liquid dispenser is a hand held pipettor, whereby the receiving movement of the suction plunger is effected manually by a user.

4. A method for pipetting a sample with a liquid dispenser comprising a body part;

a cylinder part arranged inside the body part;

a tip disposed at an end of the cylinder part;

a suction plunger movably arranged inside the cylinder part; and a function plunger disposed at an upper part of the body part of the liquid dispenser and detachably connectable to the suction plunger, wherein the method comprises:

receiving the sample into the tip of the liquid dispenser by moving the function plunger in a connected state with the suction plunger in a suction movement at a first speed; and dispensing the sample from the tip of the liquid dispenser by moving the suction plunger in a disconnected state from the function plunger in an emptying movement at a second speed greater than the first speed, wherein the method further comprises storing a mechanical energy to be provided to the suction plunger during the emptying movement in an energy storage device, prior to receiving the sample;

locking the energy storing device from releasing the energy with a locking device; and releasing the stored energy with a launch device such that the energy is provided to move the suction plunger during the emptying movement, wherein said energy storing device comprises a spring;

said locking device comprises a magnet; and said launch device comprises an actuator shaft with a magnetic property and which has a lower part and an upper part, wherein the actuator shaft is disposed such that the lower part of the actuator shaft is connected to the suction plunger and the upper part of the actuator shaft is connectable to a lower part of the function plunger via the magnet;

a launch body which accommodates the upper part of the actuator shaft and the magnet;

a launch pin disposed at an upper part of the launch body; and an upper flange disposed in the upper part of the body part, wherein the suction plunger is disposed at a lower part of the body part, the spring is arranged to be strained between the launch body and the actuator shaft, and wherein the method further comprises:

when receiving the sample, moving the function plunger upward when the magnet is in connection with an actuator shaft of the launch device;

when dispensing the sample, moving the function plunger such that the launch pin contacts the upper flange; and continuing the upward movement of the function plunger until the launch pin releases the actuator shaft from the magnet, whereby the spring forces the actuator shaft in a downward movement to effect the emptying movement of the suction plunger at the second speed.

* * * * *